United States Patent
Branković et al.

(10) Patent No.: US 9,862,271 B2
(45) Date of Patent: Jan. 9, 2018

(54) MM-WAVE RADAR DRIVER FATIGUE SENSOR APPARATUS

(71) Applicant: NOVELIC D.O.O., Belgrade (RS)

(72) Inventors: Veselin Branković, Belgrade (RS); Dušan Grujić, Belgrade (RS); Pavle Jovanović, Belgrade (RS); Veljko Mihajlović, Belgrade (RS); Milan Savić, Belgrade (RS); Darko Tasovac, Belgrade (RS)

(73) Assignee: NOVELIC D.O.O., Belgrade (RS)

( * ) Notice: Subject to any disclaimer, the term of this patent is extended or adjusted under 35 U.S.C. 154(b) by 0 days.

(21) Appl. No.: 15/303,237

(22) PCT Filed: Apr. 15, 2015

(86) PCT No.: PCT/RS2015/000009
§ 371 (c)(1),
(2) Date: Oct. 11, 2016

(87) PCT Pub. No.: WO2015/160272
PCT Pub. Date: Oct. 22, 2015

(65) Prior Publication Data
US 2017/0036541 A1    Feb. 9, 2017

(30) Foreign Application Priority Data
Apr. 14, 2014   (RS) .................... 2014/0182

(51) Int. Cl.
*G08B 23/00* (2006.01)
*B60K 28/06* (2006.01)
(Continued)

(52) U.S. Cl.
CPC .......... *B60K 28/066* (2013.01); *A61B 5/0507* (2013.01); *A61B 5/18* (2013.01);
(Continued)

(58) Field of Classification Search
CPC .... B60K 28/066; H01Q 9/285; A61B 5/0507; A61B 5/18; A61B 5/6893; A61B 5/746
(Continued)

(56) References Cited

U.S. PATENT DOCUMENTS 6,661,345 B1   12/2003   Bevan
2005/0073424 A1   4/2005   Ruoss
(Continued)

*Primary Examiner* — Toan N Pham
(74) *Attorney, Agent, or Firm* — Luoh J. Wu; Continent Patent Office LLP

(57) ABSTRACT

The present invention discloses a mm-wave radar sensor to be deployed in the vehicles for sensing driver fatigue. The key system relevant components are utilization of mm-wave integrated radar, with specific planar high gain antenna radiation pattern, by analyzing at least two major biometric parameters of the drives simultaneously: heartbeat and respiratory dynamics. The method of operation calculates probability of the fatigue event. In case that probability is above a predefined threshold, the interaction with vehicle control system is initiated, using typical arbitrary automotive interfaces. Corresponding predefined actions are taken in that case. The predefined actions could be one or combination of the following: driver safety belt pulling, audio signal alerts to driver, vibration alert to driver, inside cabin light condition changes, engine operation condition change, corresponding communication using arbitrary wireless means to outside vehicle environment. Optionally, the system is utilizing additional driver imposed parameters like acceleration sensor information. Preferably, the system is using 60 GHz or 77-79 GHz integrated radar front end working in Doppler operation mode, with 4×4 Tx and Rx planar radiation elements, with physical size typically in the range 4×2×1 cm, or smaller.

8 Claims, 9 Drawing Sheets

(51) Int. Cl.
*A61B 5/18* (2006.01)
*G08B 21/06* (2006.01)
*A61B 5/00* (2006.01)
*A61B 5/05* (2006.01)
*H01Q 1/22* (2006.01)
*H01Q 1/32* (2006.01)
*H01Q 21/00* (2006.01)
*H01Q 9/28* (2006.01)

(52) U.S. Cl.
CPC .......... *A61B 5/6893* (2013.01); *A61B 5/7225* (2013.01); *A61B 5/746* (2013.01); *G08B 21/06* (2013.01); *H01Q 1/2283* (2013.01); *H01Q 1/3233* (2013.01); *H01Q 1/3291* (2013.01); *H01Q 9/285* (2013.01); *H01Q 21/0006* (2013.01); *A61B 2503/22* (2013.01); *A61B 2562/0228* (2013.01)

(58) Field of Classification Search
USPC .............................................. 340/575, 573.1
See application file for complete search history.

(56) References Cited

U.S. PATENT DOCUMENTS

| | | |
|---|---|---|
| 2010/0234741 A1 | 9/2010 | Lee |
| 2012/0165622 A1 | 6/2012 | Rodriguez Ibanez |
| 2016/0033297 A1* | 2/2016 | Konishi ............. G01C 21/3685 701/31.4 |
| 2016/0354027 A1* | 12/2016 | Benson ................. A61M 21/02 |

* cited by examiner

Arrangement 1

Arrangement 2

Dipoles, arrangement and reflector

Chip connections without bond wires

Possible Sensor Module Functional Topology – Frontal view

Possible Sensor Module Functional Topology – Lateral view

MM-WAVE RADAR DRIVER FATIGUE SENSOR APPARATUS

TECHNICAL FIELD

The present invention relates to a driver fatigue sensor and decision making device comprising mm-wave radar with planar high-gain antenna systems, utilizing information extracted from simultaneous processing of both human heartbeat and breathing dynamics.

BACKGROUND ART

Driver fatigue is a very important risk in today's traffic safety. The USA National Highway Traffic Safety Administration conservatively estimates that 100,000 police-reported crashes are the direct result of driver fatigue each year in the USA. This results in an estimated 1,550 deaths, 71,000 injuries, and $12.5 billion in monetary losses each year. The means of predicting the driver fatigue are essential to reduce the loss of human lives, injuries and finally economic losses. A lot of effort in different techniques and approaches are currently undergoing, to provide the technical solutions, which must comply with functional capability to detect the driver fatigue, which is practical to use, can be integrated in the vehicle, and finally which is low-cost and compact enough to be practically deployed by the automotive industry.

The state of the art differentiate between principle approaches: evaluation of the driver behavior in vehicle, such as the movement of the driver's hands on the steering wheel, analysis of the vehicle driver behavior, analysis of the physiological status of the driver, and finally combination of the above principles. In many scientific papers in last two decades the ECG signals were used for investigations related to driver fatigue. Research of sleep behavior scientifically confirmed that the respiratory frequency can be used as a biomarker for probability driven detection of the driver fatigue. In most cases those investigations included ECG devices on human skin, and separately complicated respiratory measurement system on human head. It was also published in different scientific articles that microwave radar sensor, in the frequency range 3-30 GHz, may be used to detect the vital signs. Especially 2.4, 3-10, 24 and 60 GHz vital sign demonstrators have been publicly reported.

The following patents and patent applications published in last several years show the relevance of the topic and the state-of-the-art.

US 2013/0166217 A1, "Method and Device for fatigue detection" recent application combined ambient brightness and activity of the driver to reach the information about fatigue.

US 2008/0074618 A1, "Fatigue detection using encoded light signals", addresses eye lid movement of the driver to reach information about fatigue.

US 2012/0265080 A1, "Non-contact sensing of physiological signals", addresses movement of the body by non-contactless means, to reach information about fatigue. The electrode is configured to detect electrical signals from a surface of a subject's body without directly contacting the surface of the subject's body (i.e. via capacitive coupling).

U.S. Pat. No. 8,285,372 B2, "Alertness/drowsiness and cognitive index" addresses method of operation for driver fatigue recognition by using EEG signals obtained from the individual.

DE 102012000629 A1, "Method for detecting tiredness of driver of vehicle, involves transferring automatically detected tiredness affecting data from a mobile device to the vehicle, when the mobile terminal is communicatively coupled to the vehicle" of Volkswagen address the usage of the mobile equipment which detect the fatigue of the driver.

DE 102011104203 A1, "Device for detecting tiredness of driver of motor car, has processing unit for detecting tiredness-characterizing displacement of weight of driver of motor car, and sensor for detecting displacement of weight and arranged in seat surface" of General Motors addresses processing the information from weight sensor incorporated in the driver seat.

DE 102009046913 A1, "Method for detecting fatigue of driver of e.g. lorry during driving, involves evaluating information about steering movement and surrounding information for determining whether information about steering movement indicates fatigue of driver", of Robert Bosch GmbH involves evaluating information about steering movement and surrounding information for determining whether information about steering movement indicates fatigue of driver.

DE 102012013549 A1, "Method for determining driving state of driver of vehicle, involves obtaining number of activatable vitalization measures to reduce inattention and fatigue for performing manual selection and activation", considers the video technology for obtaining driver fatigue information.

CN 103230270 A1, "Capacitor electrode for detecting electrocardiogram signals of motorist" is utilizing driver contact with the steering wheel for the capacitor electrode ECG sensor to obtain the fatigue information.

DE 102011113100 A1, "Method for detection of ballistocardlogenic or respiratory-caused movements of person on motor vehicle seat, involves designing sensor as ballistographic sensor for detection of ballistocardiogenic or respiratory-caused movements of person" by Volkswagen involves ballistographic sensor for detection of ballistocardiogenic or respiratory-caused movements of a person, where the sensor are integrated in the driver seats. This is combined with the seat occupancy detection.

WO 2013076018 A1, "Detection of vital parameters by means of an optical sensor on the steering wheel" addresses detection device for detecting at least one vital parameter of a person in a motor vehicle with a steering wheel, comprising a finger sensor device with an optical sensor device, to address the driver fatigue.

CN 102509419 B, "Wireless driver fatigue monitoring device" is published, disclosing wireless monitoring device for driver fatigue, including microwave signal transmission for respiratory conditions detection of the driver, using 24 GHz radio. The system analyses the driver's breathing using wireless signal, and then converts it to a respiratory frequency. This information is compared to a preset threshold value in order to determine the fatigue.

SUMMARY OF INVENTION

This invention proposed apparatus 100 and method of operation for driver fatigue detection, and initialization of the related actions, improving safety.

The key system relevant components of the proposed apparatus 100 are:

High-gain planar antenna system, realized by the plurality of the technologies, with each of the transmit 21 and receiving 22 parts having more than one antenna radiation element and the radiation diagram in the direction of the driver.

Millimeter-wave radar with integrated front end on silicon 10, System on Chip, providing analog processing of the mm-wave signal, and the provision of the analog to digital conversion functionality;

Digital signal processing functionality 40, having standardized automotive physical digital interface 60, with plurality of the realization;

Mechanical assembly with power supply interface to the vehicle power supply infrastructure, containing mechanically integrated antenna, digital and analog functionalities and having mechanical connection to the vehicle body, preferably positioned opposite to the driver in the middle of the steering wheel or on the vehicle ceiling, above the visual field of the driver.

Supporting circuitry 50 as a part of apparatus 100 may include functionalities like loudspeaker and light warning source, by the plurality of the realization options, where apparatus is integrated in the vehicle steering wheel, facing the driver, with direct line-of-sight operation and where Method of Operation includes:

transmission of mm-wave signals generated in integrated mm-wave radio front end using high-gain planar antenna for transmitting mm-wave radio signals;

receiving mm-wave signals reflected from driver body using high-gain planar antenna for receiving mm-wave radio signals;

amplification of the reflected signal in integrated mm-wave radio front end;

down-conversion of the signals by mixing with the same signal of the same frequency as the transmitted signal in integrated mm-wave radio front end;

amplification of the converted signal after mixer in integrated mm-wave radio front end;

analog filtering of the signals after amplification in integrated mm-wave radio front end;

signal conditioning in integrated mm-wave radio front end for subsequent analog to digital conversion performed by analog to digital conversion entity;

digital processing of the signal in digital processing functionality, by:

extracting the heartbeat rate from the previous arbitrary processed signal;

extracting the rate of change of the heartbeat rate from the previous arbitrary processed signal;

extracting the respiratory rate from the previous arbitrary processed signal;

extracting the rate of change of the respiratory rate from the previous arbitrary processed signal;

digital processing in Driver fatigue event decision functionality which includes the following steps:

evaluation if the heartbeat rate is within the specified range;

evaluation if the respiratory rate is within the specified range;

evaluation if the rate of change of the heartbeat rate is within specified range;

evaluation if the rate of change of the respiratory rate is within specified range;

statistical evaluation of the driver heartbeat rate data history;

statistical evaluation of the driver respiratory rate data history;

time information entity which provides information on continuous driving duration, total driving duration in the last period of specified duration, e.g. in the last 24 hours, and current local time information;

provision of the current heartbeat rate by the entity of evaluation if the heartbeat rate being within the specified range and the current rate of change of the heartbeat rate by the entity of evaluation if the rate of change of the heartbeat rate being within specified range to driver statistic heartbeat rate model entity of statistical evaluation of the driver heartbeat rate data history;

provision of the current respiratory rate by the entity of evaluation if the respiratory rate being within the specified range and the current rate of change of the respiratory rate by the entity of evaluation if the rate of change of the respiratory rate being within specified range to driver statistic respiratory rate model entity of statistical evaluation of the driver respiratory rate data history;

digital processing in Driver fatigue event calculation decision functionality is performed, which:

calculates the score by processing the information provided through entities of evaluation if the heartbeat rate is within the specified range; evaluation if the respiratory rate is within the specified range; evaluation if the rate of change of the heartbeat rate is within specified range; evaluation if the rate of change of the respiratory rate is within specified range; statistical evaluation of the driver heartbeat rate data history; statistical evaluation of the driver respiratory rate data history and time information entity weighted by the specified coefficients, where the score is related to the probability of the driver fatigue event;

in case that the calculated score is above predefined threshold, decision on positive driver fatigue event is made;

in case of the positive driver fatigue event the entity of digital processing in Driver fatigue event calculation decision functionality sends the decision information and the corresponding score to the entity-of evaluation if the respiratory rate being within the specified range;

in case of the positive driver fatigue event the entity of evaluation if the respiratory rate being within the specified range initiates appropriate specified actions of the entity of providing interface to vehicle infrastructure by using typical vehicle wired interfaces and/or entity-of containing acceleration sensors and gyroscopes.

Above system further comprises entity of providing information about vehicle dynamics to driver fatigue event calculation entity, and where this information influences driver fatigue event score calculation in Method of operation, in case repeatable corrections of the vehicle direction are detected by MEMS based acceleration sensors.

Millimeter-wave front end preferably operates in 60 GHz ISM Band. The usage of the 77-79 GHz mm-wave frequency bands or higher mm-wave ISM bands is also proposed. The Rx and Tx antennas preferably have 4×4 elements, to explore the tradeoff between the size of the antenna, having impacts on the system cost and its integration in the vehicle environment, and obtaining the narrow antenna beam. The narrow antenna beam, associated with explicit high-gain antenna approach is essential feature of the system, providing limited possibility that the biometric data, i.e. heartbeats or respirations, from the person seating in the driver's vicinity is sensed. This is one of the essential innovative approaches, because it dramatically decreases the complexity of the digital processing, providing simple and low-cost apparatus. This is also an essential system-related factor, which imposes the usage of mm-wave signals for driver fatigue detection, as opposed to the state of the art where microwave frequency band 3-30 GHz are utilized.

Using mm-wave frequency band, preferably the 60 GHz ISM band, would allow three major advantages compared to the 24 GHz ISM band approach proposed in CN 102509419 B:

- The capability to have smaller dimensions of the high-gain antenna systems, meaning that, for the same radiation characteristics, 6 times less antenna surface is needed. This reduces the cost and greatly improves the compactness, hence almost eliminating practical use of the system proposed in CN 102509419 B.
- The advantage of the proposed innovation is that the utilization of the higher frequency increases the resolution of the target micro displacements, in this case a human body heartbeat and respiratory dynamics. The proposed system provides at least 3 times better resolution compared to CN 102509419 B. Moreover, micro displacement may be analyzed with increased accuracy if the IQ outputs are available, as proposed.
- The advantage of the proposed innovation is that the mm-wave frequency band signals, in applications where humans are irradiated, do not penetrate the human skin. The penetration depth is significantly lower compared to the microwave frequency band, typically 3 times shallower than in the case of state of the art CN 102509419 B.

Smaller size of the module allows physical integration in the vehicle steering wheel, which provides further system advantage by providing the direct path to the driver and also allows easier manufacturing. As an example, if the state of the art system operating in 24 GHz band would be integrated in the steering wheel, due to the size constrains, only the wide-radiation antenna systems could be used, comprising only one or two radiating elements for Rx and Tx. This would allow system to "pick up" vital signs from the persons in the driver's vicinity.

In the state of the art 24 GHz approach CN 102509419 B radio system considers one shared antenna for TX and RX part, and utilization of the circulators as well as power couplers. Our proposed mm-wave radar system has separate Tx and Rx antennas. This dramatically simplifies the complete system, and enables the use in the vehicle environment by avoiding the expensive and impractical elements like circulators. Moreover, present invention has innovative approach of integrating complete RF functionalities of the mm-wave radar (30-300 GHz) within a system-on-chip, including complete mm-wave frequency synthesis, fabricated in standard silicon process. Moreover, in contrast to CN 102509419 B, the present innovation introduces digital signal processing which allows significant system advantage of using single digital processing HW for simultaneous processing of both heartbeat and respiratory dynamics. Proposed CN 102509419 B topology would require twice the processing HW complexity to process both biomarkers, has no inherent signal processing capability to filter out signals from two sources, and cannot add specific adjustments in averaging procedures, which may be required for system customization for the particular vehicle cabin environment.

As a significant innovation step, in contrast to the state-of-the-art, the proposed system analyses both biomarkers simultaneously, thereby dramatically increasing the accuracy of fatigue detection and decreasing the probability of the false alarm.

The proposed apparatus has significant advantages compared to the state-of-the-art, in at least of one of the following features:

- There is no physical contact to the driver or driver's clothes.
- The system functions independently of the light condition in the vehicle cabin.
- The system is inherently low-cost allowing the complete HW solution in the range less than 10$ for large quantities.
- The system is compact with inherently small thickness of typically less than 1 cm, allowing easy integration, which reduces assembly cost in the vehicle manufacturing, and allows aftermarket deployment
- The system analyzes two essential biomarkers simultaneously: heartbeat and respiratory dynamics, and therefore has increased accuracy in driver fatigue detection, i.e. small probability of the false alarm, which presents unique advantage over all known state-of-the-art solutions for driver fatigue detection.

The proposed system may function with several meters distance between the driver and the apparatus, depending on the antenna arrangement, transmit power, and receiver sensitivity. The transmit power is, however, reduced to the minimum needed, for the reasons of having minimum power consumption, minimum thermal dissipation, and minimum reflection clutters, which will further simplify digital processing algorithms and further reduce the power consumption and thermal dissipation. The digital part has typical CAN and/or LIN interface allowing easy connection to vehicle infrastructure. The means of short range wireless connection to the vehicle system 63 is optional and suited for the aftermarket usage.

Apparatus 100 could be also realized with one high gain planar antenna and isolator functionality. This may reduce the size of the system but in the same time increase the technical requirements on isolator functionality, which is difficult to release in the low cost and miniature manner.

Instead of the down conversion mixer in the integrated mm-wave chip functionality 10, the IQ demodulator may be integrated, providing some extra features in the digital signal processing.

DESCRIPTION OF EMBODIMENTS

Figure 1:
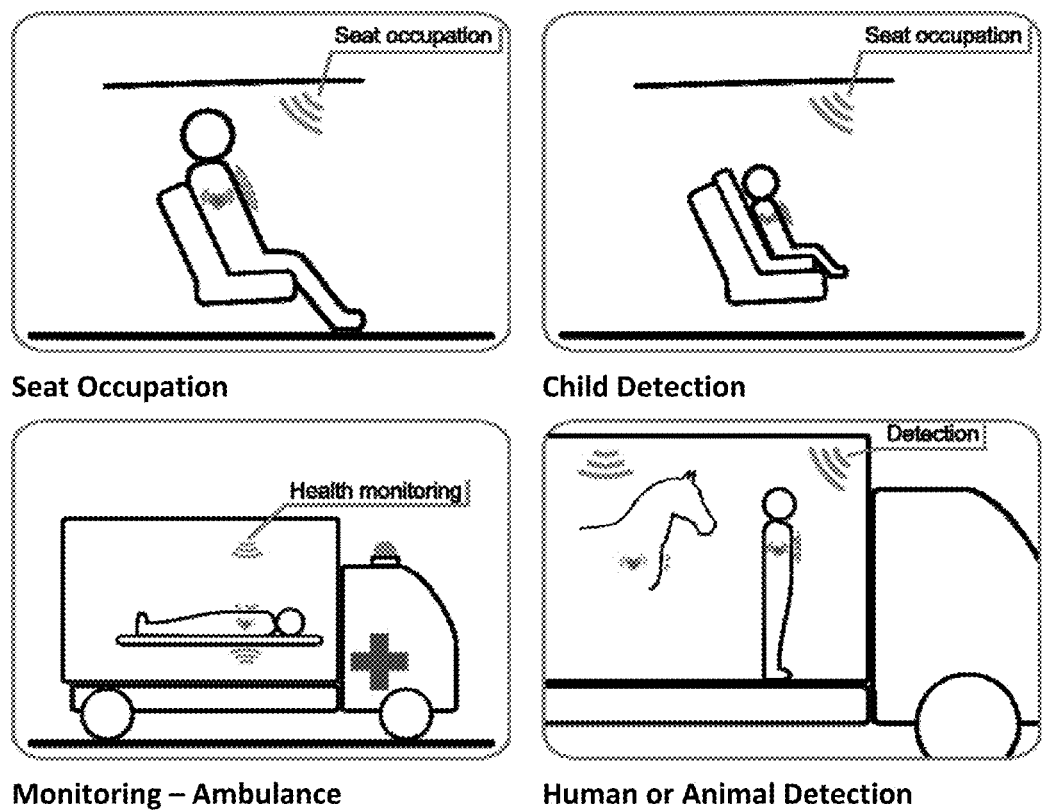
FIG. 1 presents apparatus in the vehicle environment—application scenarios
Figure 2:
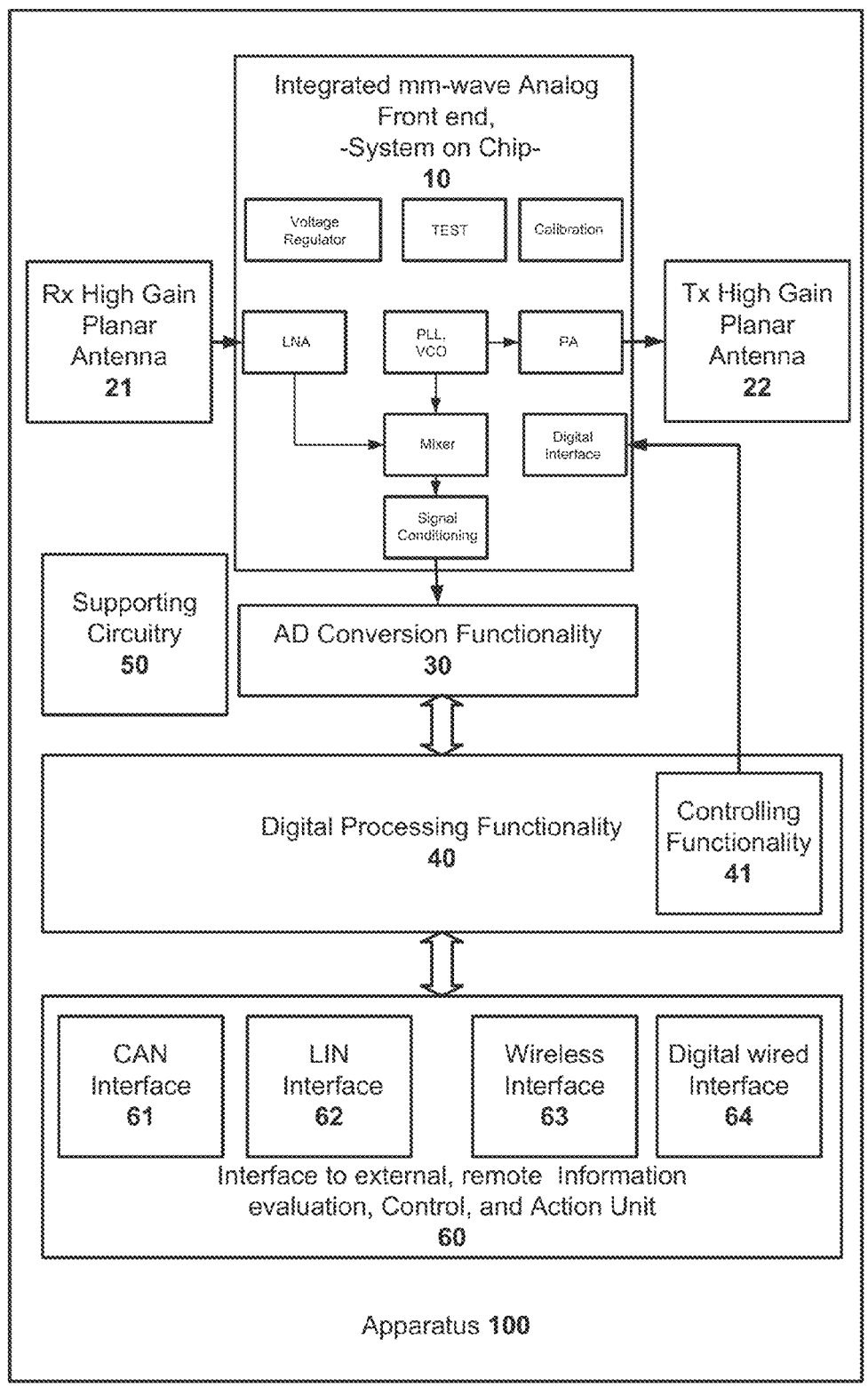
FIG. 2 presents apparatus functional block diagram
Figure 4:
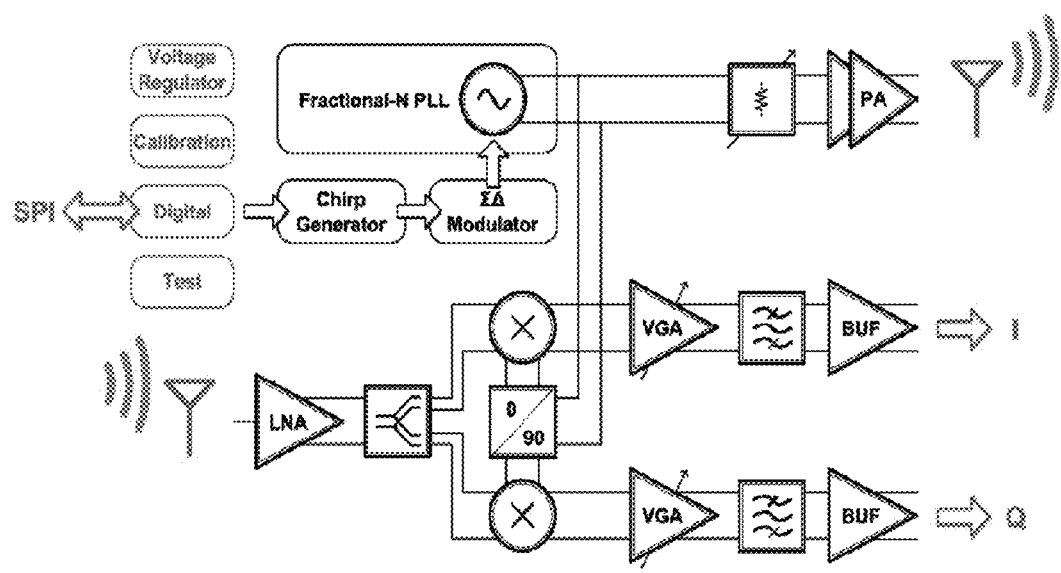
FIG. 4 presents integrated mm-wave front end block diagram

Apparatus 100 is integrated preferably in the steering wheel of the vehicle as shown in the FIG. 1. Alternatively, the Apparatus 100 is placed on the vehicle chassis, above visual field of the driver having LOS connection to the driver body, as shown in FIG. 1. Due to advantageously proposed mm-wave radar application, the size of the high-gain Antenna System for Rx 21 and for Tx 22 is small enough to allow practical use of the apparatus in the vehicle cabin while maintaining high-gain antenna features. Taking into account proposed 60 GHz ISM band operation, or alternatively 77-79 GHz operation, and 4×4 antenna elements for 21 and 22, the approximate size of the device may be less than 4×2×1 cm, which would inherently allow practical use in vehicle cabins. The crucial block of the proposed apparatus 100 is the Integrated mm-wave front end, System on Chip 10. It contains the complete RF functionality, and includes power amplifier functionality attached to the antenna system 22, low noise amplifier attached to antenna system 21, integrated PLL, used both for up-conversion in transmit and down-conversion in receive, one analog pre filtered an amplified signal or providing two analog pre-filtered and amplified signals as IQ outputs to A/D conversion functionality 30. The entity 10 has test functionality, voltage regulation, and digital interface to the Controlling functionality 41, which is a part of the Digital Processing functionality 40. More detailed structure of the integrated front end 10 is given in FIG. 4, with IQ outputs. The realization with one down conversion mixer and one signal conditioning part compromising amplification and filtering, would require less space in the entity 10 and therefore less cost. The use of the integrated front end 10 allows the system to be compact and have low-cost assembly, enabling the use in the real product. Integration of the complete frequency synthesis and complete analog functionality in a single chip allows considerable reduction of the cost, which is not the case in published mm-wave systems. The entity 10 is preferably realized using SiGe BICMOS technology that provides high performance. Alternatively CMOS technology may be used. AD (analog to digital) conversion functionality 30 converts the analog conditioned signal or two quadrature signals, I and Q, of the entity 10, and feeds digital representation of signal or signals to the Digital processing functionality 40 for further processing. Entity 30 is realized by plurality of the realization options, with sampling frequency typically under 1 MHz and typically at least 8 bit resolution for the vital signs detection applications. Entity 30 may be integrated on the same chip as Entity 10. Entity 30 may be integrated on the same chip as Entity 40. Entities 40, 10, and 30 may be all integrated on a single chip. Entity 60 may provide interface to vehicle infrastructure by using typical vehicle wired interfaces like CAN interface 61, and/or UN interface 62, optional custom digital interface 64, and optional short range wireless interface 63. Standard interface, preferably CAN, is preferred for all applications where the apparatus is integrated in vehicle during manufacturing. For aftermarket applications the short range wireless interface, preferable Bluetooth, may be integrated in entity 60. Supporting circuitry 50 optionally includes additional memory, manual switching, power supply regulation circuitry, mechanical support, and any additional functionality required for easy integration, during manufacturing or later in aftermarket. The mechanical support structure for integration of all functionality is preferably provided using advanced polymer technologies. Optionally entity 60 may contain acceleration sensors and gyroscopes, preferable realized by MEMS technologies, providing additional information of the vehicle dynamics to entity 40, which also may be used for detection of driver fatigue event. Optionally, in case of the aftermarket operation, entity 50 may also include battery, loudspeaker or warning light sources, allowing autonomous operation.

Figure 3:
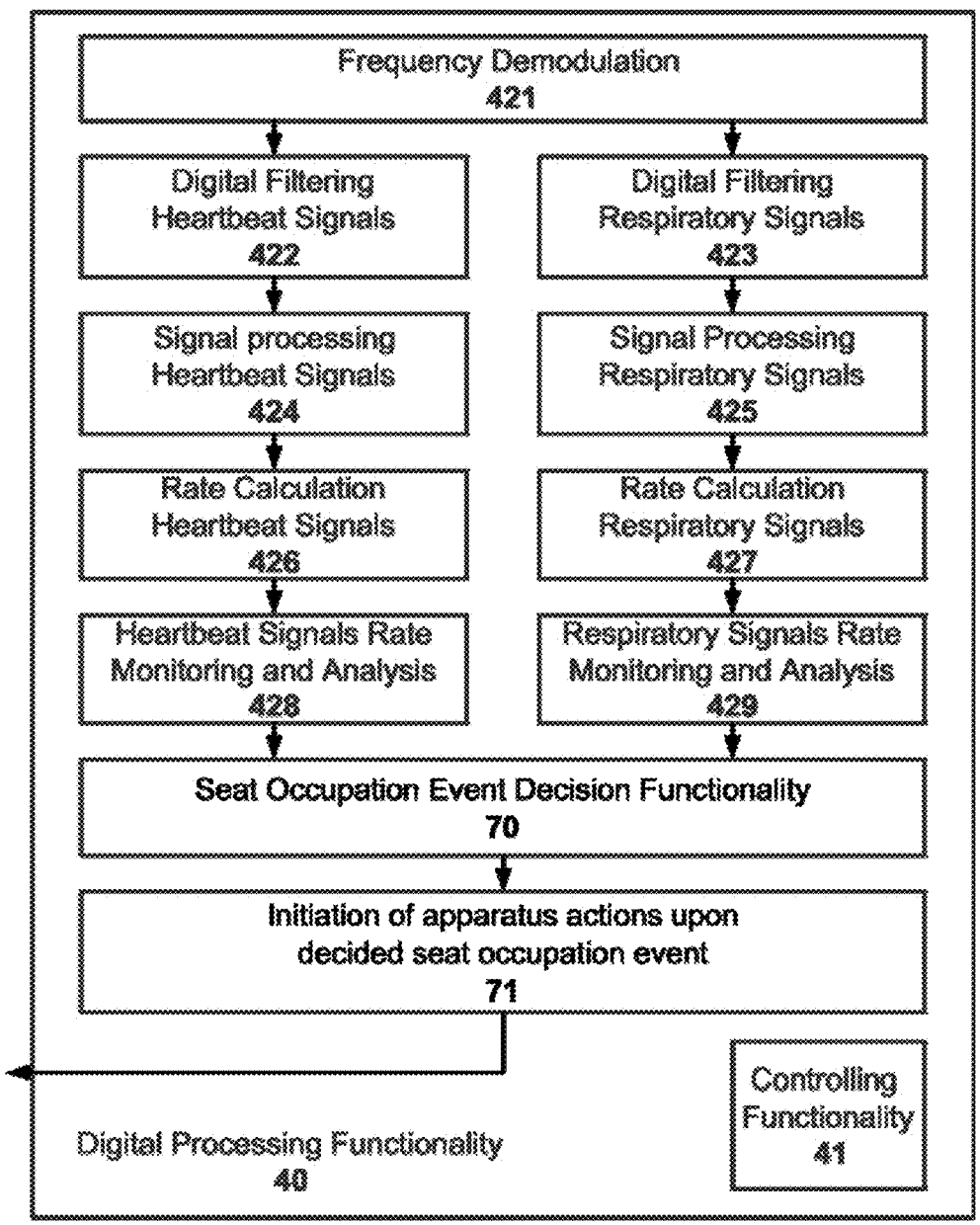
FIG. 3 presents apparatus digital processing functional blocks

Digital processing functionality 40 may be realized by the plurality of technologies, such as: advanced CPUs, FPGAs, advanced μC, DSP, or ASIC, or their combinations, where the digital processing may be performed by "soft" approach or by hard-wired approach or by their combination. Preferably functionalities 60 and 40 are integrated on a simple ASIC, having CPU on one digital SOC. Digital processing functionality 40 includes functionalities 41, 421-429 and 70-71 as described in FIG. 3. The goal is to perform remote and contactless detection of the driver body movement. Important information is the micro-movement of the driver's body; therefore, the simplest approach like Doppler radar system may be used. The entity 10 sends mm-wave CW signal by Tx antenna entity 22 towards the driver's body. The radio signal of mm-wave frequency does not penetrate the clothes and the human body. Heartbeat and respirations cause body micro-movements. According to Doppler effect those movements are causing frequency modulation of the radio signal received by the antenna entity 21. After the downconversion or IQ demodulation, i.e. mixing with the quadrature of the transmitted signal, and subsequent filtering, and amplification performed in the entity 10, the low-frequency baseband signal or signals are provided to the entity 30. These analog signal or two analog signals are converted into corresponding one or two digital streams by the entity 30 and fed into the entity 40. In entity 421 additional low-pass digital filtering may be performed. Data is further provided to entities 422 and 423, which perform appropriate digital band-pass filtering such that the expected heartbeat and respiratory rates are in-band. Filter characteristics must account for the expected variations of the appropriate biomarkers which reflect normal and fatigue conditions. Filtering characteristics may be set based on the driver biomarkers history and statistics, previously stored in memory. Entities 426 and 427 perform the calculation of the heartbeat and respiration rates, respectively. Filtered signals are first converted in the frequency domain. The corresponding heartbeat and respiratory rates are detected as peaks in signal spectrum. The position of the peaks determines the corresponding rate. The plurality of peak detection methods may be utilized, with corresponding digital signal processing realizations of various averaging, smoothing, windowing and peak position estimation techniques. In entities 428 and 429, the calculated rates are further processed by calculating the rate of the change of the heartbeat and respiratory rates, which may be mathematically expressed as derivatives of the corresponding biometric rates, where various averaging techniques may be applied. This information is provided to the entity 70, which is responsible for driver fatigue detection. In entities 711 and 712 respective rates are compared with the set of previously detected values, or predefined thresholds, which are provided by entities 715 and 716. All information is provided to the entity 720. Entities 715 and 716 are updated with the new rates and corresponding rates of change. Entities 715 and 716 contain the history of the driver biomarkers information, particularly including:

Rate information in specific predefined time steps

Averaged information of rate over at least one predefined period

Rate of change information in specific predefined time steps

Averaged Information of rate of change over at least one predefined period

Comparison thresholds for rate
Compassion thresholds for rate of change
Comparison thresholds may be predefined or statistically calculated based on the stored data.

In particular, entities 715 and 716 have models and ranges for biomarkers rates and biomarker rate of change, representing "awake" or "drowsy" status. Time information entity 717 is providing additional information to entity 720 including:
 information about the total driving duration in the last period of the specified duration, e.g. in the last 24 hours;
 information about continuous driving duration;
 current local time information.

Optional entity 719 is providing information form the external cabin gas sensor to entity 720, preferably including $CO_2$ concentration. Optional entity 718 provides information on vehicle dynamics to entity 720. This information may be calculated based on data from MEMS sensors in the entity 50 or data from external sensors embedded in vehicle provided to apparatus 100 through entity 60. Driver fatigue event calculation entity 720 is calculating the driver fatigue event score based on a weighted sum of the following information set:
 Heartbeat rate value reduced below calculated or predefined threshold.
 Rate of change of the heartbeat rate achieved calculated or predefined threshold.
 Respiratory rate value reduced below calculated or predefined threshold.
 Rate of change of the respiratory rate achieved calculated or predefined threshold.
 Duration of the continuous driving above calculated or predefined threshold.
 Duration of the drive in predefined time frame above calculated or predefined threshold.
 Part of the day: early morning, daytime, twilight, night, late night.

The weighting factors are predefined or determined based on the information set, predefined values and driver behavior statistics. If the score is above the threshold, the event of driver fatigue is detected. Based on the score value, the fatigue category is determined. This information is communicated to the entity 71. Based on this information, the entity 71 is initiating predefined actions using entity 60 and/or entity 50 where optional audio and visual alerting capability is included. Predefined fatigue categories are:
 Very high probability of driver fatigue event, Event A
 High probability of driver fatigue event, Event A
 Moderate probability of driver fatigue event, Event C Event A may be related to immediate audio alerts, light alerts, optional activities related to engine and/or brakes control, e.g. short braking actions with the goal of waking up the driver by the mechanical stress, optional video alert on multimedia console, optional update of driver status information, optional communication to remote fleet or traffic management. Event B may be related to immediate audio alerts, light alerts, optional video alert on multimedia console, optional update of the driver status information, or communication to the remote fleet or traffic management. Event C may be related to immediate audio alerts, light alerts.

If the apparatus detects the abrupt stop of the heartbeat confirmed with the cease of respiratory activity, alerts to the driver are initiated. In case the driver does not respond, emergency condition is confirmed and emergency actions are initiated. Emergency actions may include appropriate engine and/or brake systems control, and/or emergency calls.

Figure 5:
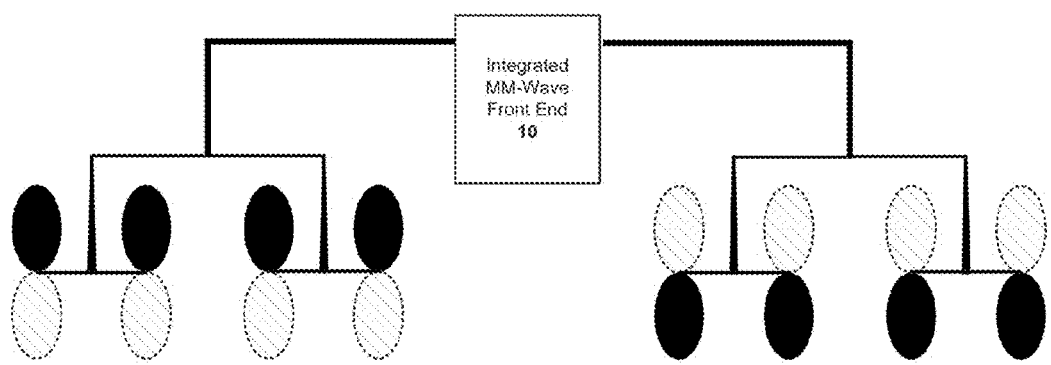
FIG. 5 presents antenna Rx and Tx system options with 4 and 8 dipoles
Figure 5:
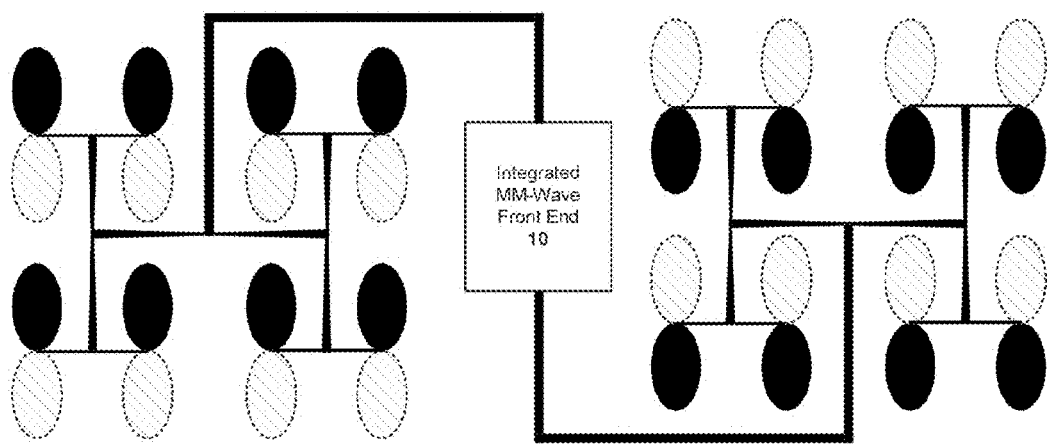
Figure 6:
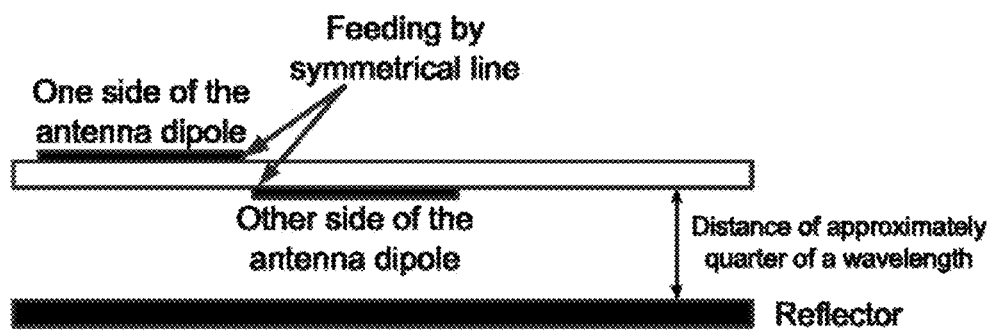
FIG. 6 presents antenna element arrangement and chip connection to the antenna feeding arrangement
Figure 6:
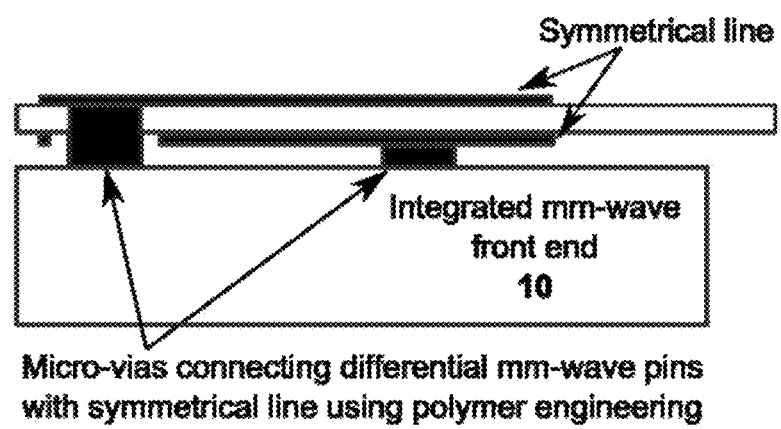
Figure 7:
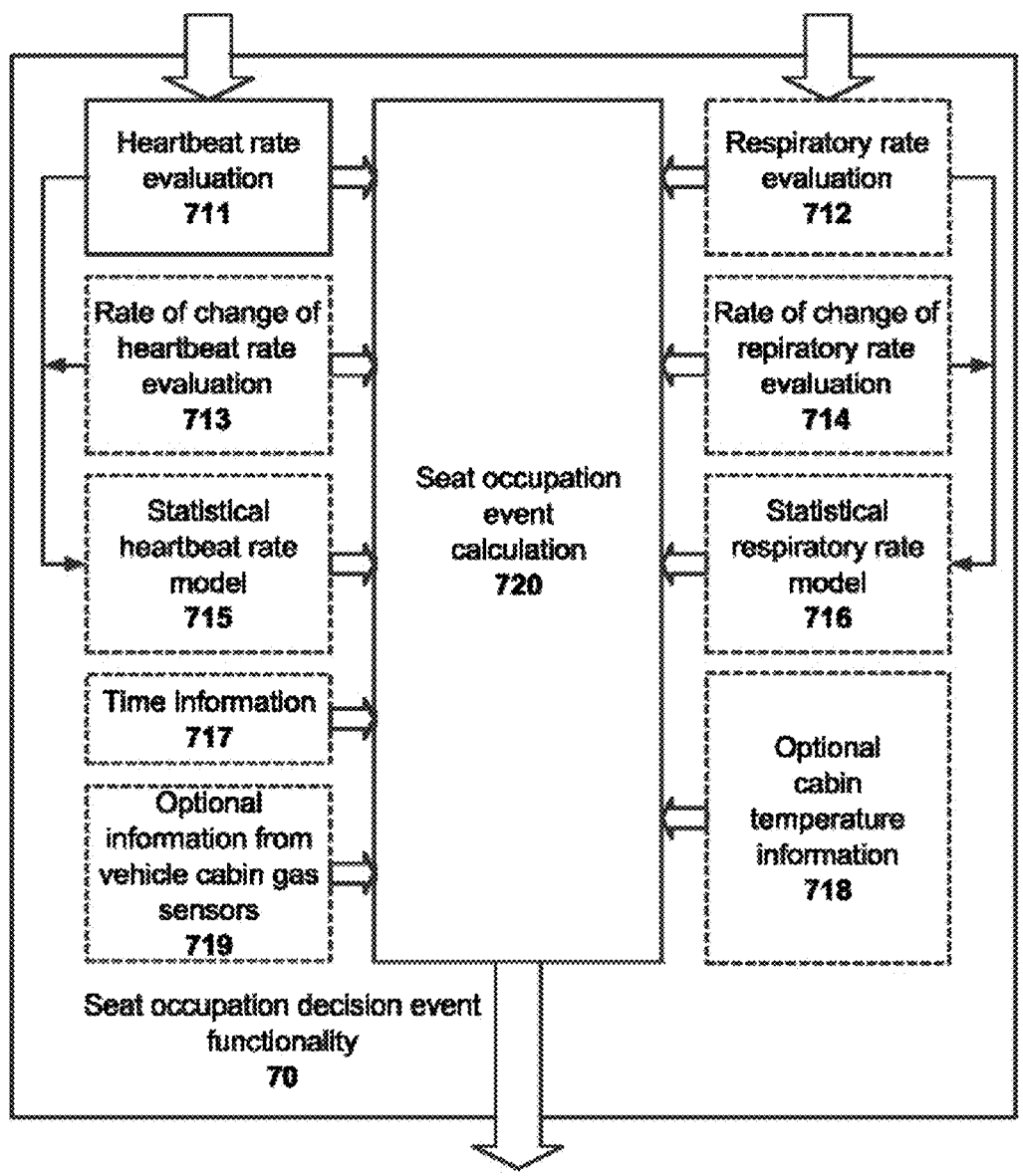
FIG. 7 presents driver fatigue event detection functional block
Figure 8:
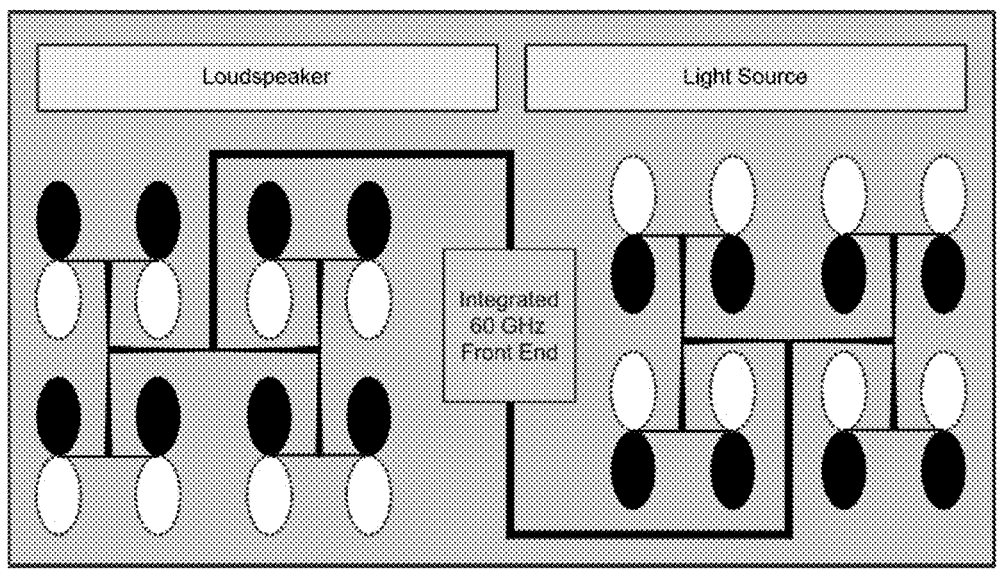
FIG. 8 presents preferable integrated module 3D topology based on apparatus 100, top and lateral view, with polymer integration approach FIG. 9*a*) presents apparatus functional block diagram with one high gain antenna for both transmitting and receiving mm-wave radio signals, isolator functionality and single mixer in mm-wave chip functionality 10
Figure 8:
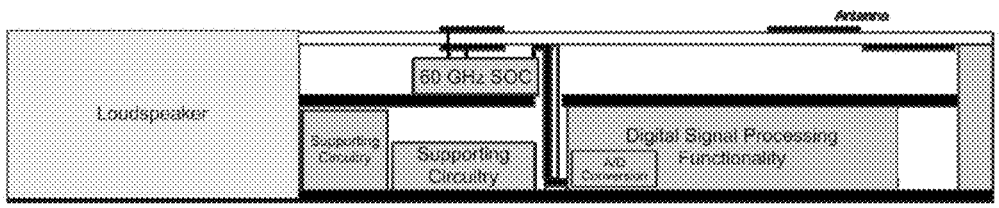

In FIG. 5 two antenna high-gain arrangements are shown. Systems 21 and 22 are on the left and right side of the integrated front end entity 10. The arrangement 2 may be considered as the preferred embodiment, providing preferable tradeoff in size and performance, having the front size dimensions of the complete apparatus 100 of 4×2 cm or less for the 60 GHz ISM band operation. The antenna system is preferably realized as the planar printed dipoles with ellipsoid-like antenna shapes, with the two parts printed on opposite sides of the dielectric layer, which also provides mechanical support. Prints on the opposite side of the dielectric are depicted using dashed lines on FIG. 5. Cross section presented in FIG. 6 shows antenna printed on the opposite sides of the dielectric layer, as well as metalized reflector at the distance of approximately one quarter of wavelength. The space between the reflector and the antenna may be empty or filled with foam. The antenna parts 21 and 22 are fed by the symmetrical lines printed on both sides of the dielectric approaching dipoles perpendicularly to their arrangement, as shown in FIG. 5. Symmetrical line may be advantageously connected to differential mm-wave inputs and outputs of the entity 10 by using micro-vias produced by an advanced polymer technology. This is illustrated in of FIG. 6.

Supporting circuitry 50 as a part of the apparatus 100 may include loudspeaker functionality having plurality of possible realizations. This feature would allow apparatus 100 to be independent of the vehicle infrastructure by initializing audio warnings in case of the driver fatigue detection. Supporting circuitry 50 as a part of the apparatus 100 may include light warning source functionality having plurality of possible realizations. This feature would allow apparatus 100 to be independent of the vehicle infrastructure by initializing light warnings in case of the driver fatigue detection. These options are useful for all types of the aftermarket applications, where the apparatus 100 is assembled in vehicles after production.

Figure 9:
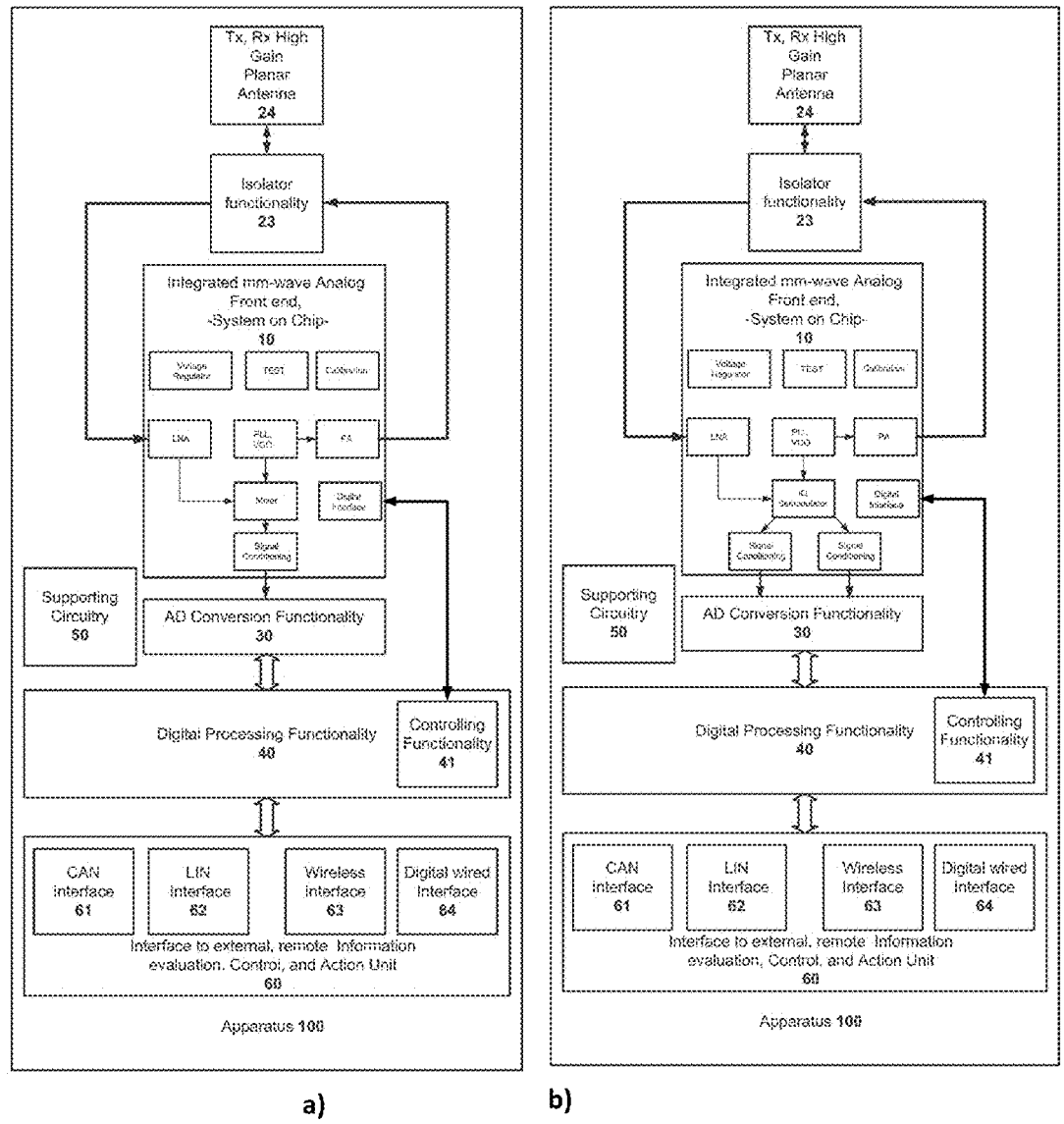
FIG. 9*b*) presents apparatus functional block diagram with one high gain antenna for both transmitting and receiving mm-wave radio signals, isolator functionality and IQ demodulator in mm-wave chip functionality 10

Alternatively instead of using two high gain antennas one for Tx 22 and one for Rx 21, the proposed system may be realized by one high gain antenna for both Rx and Tx functionality, 24 like in FIG. 9a) and FIG. 9b) and isolator functionality 23. This approach has several system disadvantages of the difficult practical realization of the entity 23 providing sufficient isolation between Rx and TX inputs of the entity 10. Also entity 23 inherently includes unwanted signal attenuation of the TX signal toward antenna and received signal from antenna toward the RX input of the entity 10. This imposes more power consumption of the system, more thermal dissipation, and more system cost on isolator entity 23 realization. Entity 23 could be preferably realized by rat race planner coupler structures, also on the IC level within the entity 10 or on the PCB level, where the entity 10 is assembled in the Apparatus 100. The only potential system related sensor advantage would be the reduced size of the apparatus 100, where the one planar high gain antenna would need to be integrated instead of two. The usage of the IQ demodulator instead of signal mixer in entity 10, would provide the two analog baseband down converted quadrature signals to the entity 30. Having two signals in the signal processing path additional information about phase changes between two signal may be used. This may increase the accuracy in the digital signal processing and some redundancy, by the expense of the more chip size of entity 10 and more processing efforts of the entity 40. The method of operation may use the straight forward information obtained from the one down conversion chain from I or from Q chain, and do not process the information from other chain, as long there is no need in more accurate information extraction. The existence of the both chains, with 90 degrees moved zero crossings, may have practical advantages. By evaluating the phase changes of the IQ signals, with the typical accuracy of 1-2 degrees resolution, micro movements of the objects may be evaluated with more accuracy, within one wave length typically in μm region. This may increase the capability of the frequency extraction.

The invention claimed is:

1. Mm-wave Radar Driver Fatigue Sensor Apparatus and Method of Operation, where mm-wave declares operation between 30 and 300 GHz, including:
   high-gain planar antenna for transmitting mm-wave radio signals, where the high-gain planar antenna has at least two radiation elements;
   high-gain planar antenna for receiving mm-wave radio signals, where the high-gain planar antenna has at least two radiation elements;
   integrated mm-wave radio front end, implemented in arbitrary semiconductor technology, having on-chip integrated mm-wave voltage control oscillator, mm-wave power amplifier, mm-wave low noise amplifier, mm-wave mixer, digital control interface, power supply; and PLL analog to digital conversion entity;
   digital processing functionality including controlling functionality and calculation and memory capacity for performing digital signal processing by arbitrary type of the realization options;
   optional interface to vehicle infrastructure, including one or more standardized automotive wired interfaces;
   supporting circuitry, including mechanical interface to vehicle infrastructure and supporting electronic circuitry for power supply of apparatus;
   where the apparatus is integrated in a vehicle steering wheel, facing a driver, with direct line-of-sight operation and where Method of Operation includes:
   transmission of mm-wave signals generated in integrated mm-wave radio front end using high-gain planar antenna for transmitting mm-wave radio signals;
   receiving mm-wave signals reflected from driver body using high-gain planar antenna for receiving mm-wave radio signals;
   amplification of the reflected signal in integrated mm-wave radio front end;
   down-conversion of the signals by mixing with the same signal of the same frequency as the transmitted signal in integrated mm-wave radio front end;
   amplification of a converted signal after mixer in integrated mm-wave radio front end;
   analog filtering of the signals after amplification in integrated mm-wave radio front end;
   signal conditioning in integrated mm-wave radio front end for subsequent analog to digital conversion performed by analog to digital conversion entity;
   digital processing of the signal in digital processing functionality, by:
   extracting a heartbeat rate from the previous arbitrary processed signal;
   extracting a rate of change of the heartbeat rate from the previous arbitrary processed signal;
   extracting a respiratory rate from the previous arbitrary processed signal;
   extracting a rate of change of the respiratory rate from the previous arbitrary processed signal;
   digital processing in driver fatigue event decision functionality which includes the following steps:
   evaluation if the heartbeat rate is within a specified range;
   evaluation if the respiratory rate is within a specified range;
   evaluation if the rate of change of the heartbeat rate is within the specified range;
   evaluation if the rate of change of the respiratory rate is within the specified range;
   statistical evaluation of a driver heartbeat rate data history;
   statistical evaluation of a driver respiratory rate data history;
   time information entity which provides information on continuous driving duration, total driving duration in last period of specified duration and current local time information;
   provision of a current heartbeat rate by the entity of evaluation if the heartbeat rate being within the specified range and the current rate of change of the heartbeat rate by the entity of evaluation if the rate of change of the heartbeat rate being within the specified range to driver statistic heartbeat rate model entity of the statistical evaluation of the driver heartbeat rate data history;
   provision of a current respiratory rate by the entity of evaluation if the respiratory rate being within the specified range and the current rate of change of the respiratory rate by the entity of evaluation if the rate of change of the respiratory rate being within the specified range to driver statistic respiratory rate model entity of the statistical evaluation of the driver respiratory rate data history;
   digital processing in Driver fatigue event calculation decision functionality is performed, which:
   calculates a score by processing the information provided through entities of evaluation if the heartbeat rate is within the specified range; evaluation if the respiratory rate is within the specified range; evaluation if the rate of change of the heartbeat rate is within specified range; evaluation if the rate of change of the respiratory rate is within specified range; statistical evaluation of the driver heartbeat rate data history statistical evaluation of the driver respiratory rate data history and time information entity weighted by a specified coefficients, where the score is related to a probability of the driver fatigue event;
   in case that the calculated score is above predefined threshold, decision on positive driver fatigue event is made;
   in case of a positive driver fatigue event the entity of digital processing in Driver fatigue event calculation decision functionality sends the decision information and the corresponding score to the entity of evaluation if the respiratory rate being within the specified range;
   in case of the positive driver fatigue event the entity of evaluation if the respiratory rate being within the specified range initiates appropriate specified actions of the entity of providing interface to vehicle infrastructure by using typical vehicle wired interfaces and/or entity of containing acceleration sensors and gyroscopes.

2. System according to claim 1, in which apparatus is integrated in a vehicle chassis above the driver's visual field, facing the driver, with direct line-of-sight operation.

3. System according to claim 1, in which further comprises entity of providing information about vehicle dynamics to driver fatigue event calculation entity, and where this information influences driver fatigue event score calculation in method of operation, in case that the reduction of vehicle speed is detected by MEMS based acceleration sensors.

4. System according to claim 1, in which further comprises entity provides of providing information about vehicle dynamics to driver fatigue event calculation entity, and where this information influences driver fatigue event score calculation in Method of operation, in case repeatable corrections of a vehicle direction are detected by MEMS based acceleration sensors.

5. System a according to claim 1, in which optional information from vehicle cabin gas sensor is provided to driver fatigue event calculation entity, and where this information influences driver fatigue event score calculation in method of operation, in case that increased $CO_2$ concentration is detected.

6. System according to claim 1, in which the supporting circuitry contains audio and/or visual alerting capabilities of arbitrary realization, which are activated in case the driver fatigue event is detected by the entity of initiating predefined actions.

7. System according to claim 1, in which the sensor apparatus and method of operation has only one high gain antenna for transmitting and receiving mm-wave radio signals, where the high-gain planar antenna has at least two radiation elements and isolator functionality being released by plurality of the realization option, providing isolation between Rx and Tx chains, and related Rx and Tx connection to high gain antenna.

8. System according to claim 1, in which the sensor apparatus and method of operation has entity of integrated mm-wave radio front end having instead of mm-wave down conversion mixer, an IQ Demodulator, and two signal conditioning chains instead of one.

* * * * *